US006907880B1

(12) United States Patent
Heckenmüller et al.

(10) Patent No.: US 6,907,880 B1
(45) Date of Patent: Jun. 21, 2005

(54) INHALATION DEVICE

(75) Inventors: Harald Heckenmüller, Hamburg (DE); Ulrich Hetzer, Rellingen (DE); Heike Kublik, Hamburg (DE); Alfred von Schuckmann, Kevelaer (DE); Volker Tiedemann, Itzehoe (DE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/646,140

(22) PCT Filed: Mar. 16, 1999

(86) PCT No.: PCT/SE99/00416

§ 371 (c)(1),
(2), (4) Date: May 10, 2002

(87) PCT Pub. No.: WO99/47099

PCT Pub. Date: Sep. 23, 1999

(30) Foreign Application Priority Data

Mar. 17, 1998 (SE) .................................. 9800897

(51) Int. Cl.⁷ ............................................ B65D 83/06
(52) U.S. Cl. ..................... 128/203.15; 128/203.12; 128/203.19; 128/23.21
(58) Field of Search ............... 128/203.12, 203.13, 128/203.19, 203.21; 206/531, 532, 538

(56) References Cited

U.S. PATENT DOCUMENTS

| 4,340,141 | A | * | 7/1982 | Fischer | 206/531 |
| 4,838,425 | A | * | 6/1989 | O'Brien et al. | 206/531 |
| 4,911,304 | A | * | 3/1990 | Bunin | 206/531 |
| 5,533,502 | A | * | 7/1996 | Piper | 128/203.21 |
| 5,595,175 | A | * | 1/1997 | Malcher et al. | 128/203.15 |
| 5,695,063 | A | * | 12/1997 | Roulin et al. | 206/531 |
| 5,794,781 | A | * | 8/1998 | Roulin et al. | 206/531 |
| 5,819,940 | A | * | 10/1998 | Roulin et al. | 206/531 |
| 5,904,249 | A | * | 5/1999 | Roulin et al. | 206/531 |
| 6,024,222 | A | * | 2/2000 | Friberg et al. | 206/531 |
| 6,401,712 | B1 | * | 6/2002 | Von Schuckmann | 128/203.15 |
| 6,520,179 | B1 | * | 2/2003 | Von Schuckmann et al. | 128/203.15 |

FOREIGN PATENT DOCUMENTS

| WO | WO 92/04069 | 3/1992 | | |
| WO | WO 93/17728 | 9/1993 | | |
| WO | 44 29 503 A1 | 2/1996 | | |
| WO | WO 97/02061 | 1/1997 | | |
| WO | WO 97/40876 | 11/1997 | | |
| WO | WO97/40876 | * 11/1997 | ............ | 128/203.15 |
| WO | WO/98/00351 | * 1/1998 | ................ | 208/531 |

OTHER PUBLICATIONS

Copy of Search Report for Hungarian Patent Application No. P0101444.

* cited by examiner

Primary Examiner—Henry Bennett
Assistant Examiner—Amanda Wieker
(74) Attorney, Agent, or Firm—Fish & Richardson P.C.

(57) ABSTRACT

A blister pack unit for a powder inhaler, comprising a body which includes a plurality of surfaces which each includes a plurality of blisters (21, 22) containing powder containing medicament and are rotationally symmetrically disposed about an imaginary axis.

16 Claims, 13 Drawing Sheets

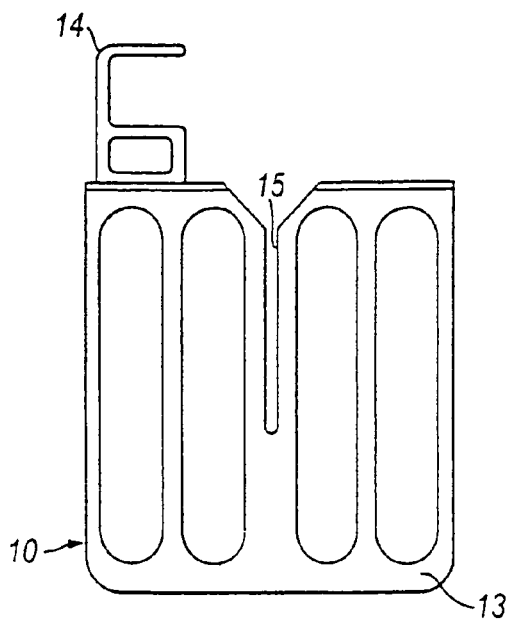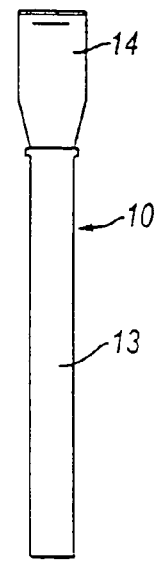
Fig.7(a)        Fig.7(b)
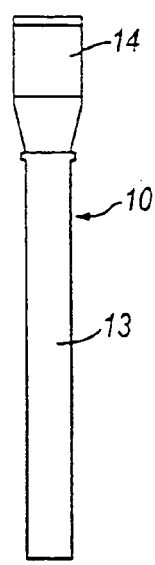
Fig.7(d)
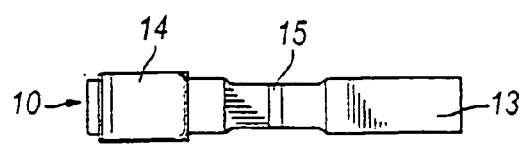
Fig.7(c)        Fig.7(e)

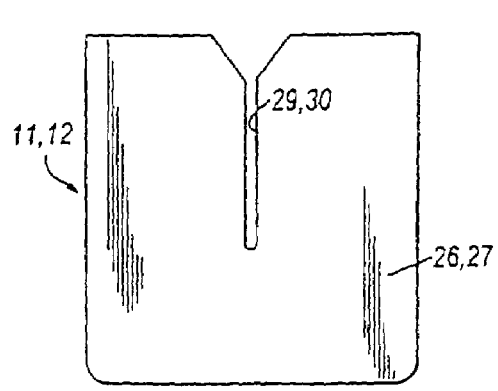
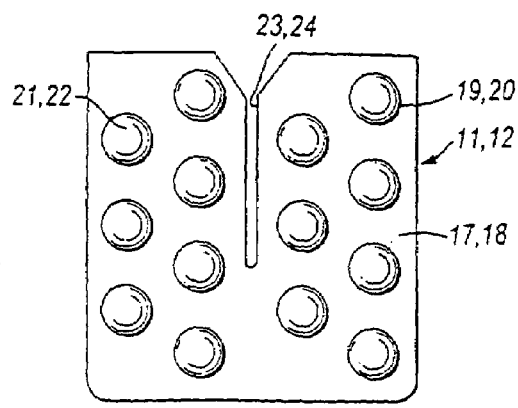
Fig.8(a)   Fig.8(b)
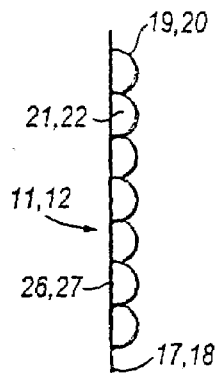
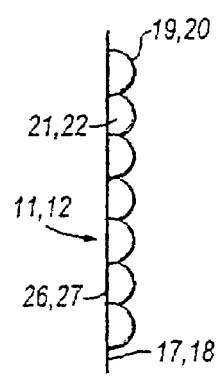
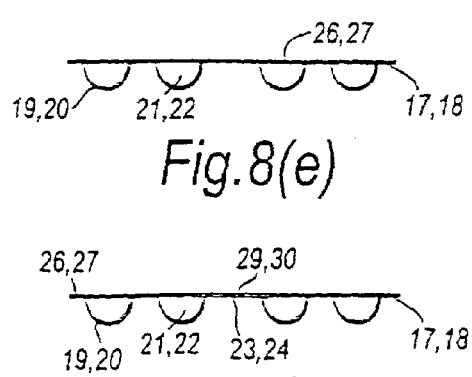
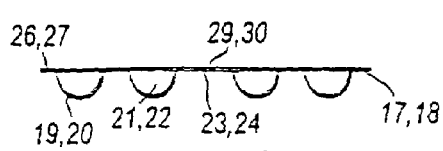
Fig.8(c)   Fig.8(d)   Fig.8(e)
Fig.8(f)
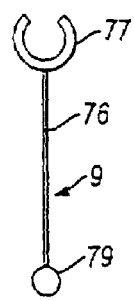
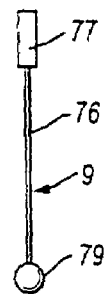
Fig.9(a)   Fig.9(b)

INHALATION DEVICE

The present invention relates to a blister pack unit for an inhaler for administering dry powder by inhalation, a blister pack assembly comprising the same and an inhaler comprising the same.

It is known in the treatment of respiratory conditions, such as asthma, to provide certain medicaments in the form of a dry powder for inhalation. It is also known to provide individual doses of such powders in the blisters of a blister pack element.

WO-A-97/40876 discloses a powder inhaler for administering dry powder which comprises a support unit for supporting a blister pack element which includes a plurality of blisters, with each blister containing a dose of powder containing medicament, and a suction tube which is configured so as to be insertable into a respective one of the blisters and through which a dose of powder is in use drawn on inhalation by a user.

Whilst this known powder inhaler functions perfectly adequately, it is an aim of the present invention to provide a blister pack unit for a powder inhaler, which, for the same number of doses, is of smaller dimension and hence provide a powder inhaler of smaller dimension.

Accordingly, the present invention provides a blister pack unit for a powder inhaler, comprising a body which includes a plurality of surfaces which each include a plurality of blisters containing powder containing medicament and are rotationally symmetrically disposed about an imaginary axis.

In a preferred embodiment the imaginary axis is an axis through the body.

Preferably, the body includes a support member which supports the plurality of surfaces.

More preferably, the support member comprises a frame.

Preferably, the body includes first and second oppositely-directed surfaces.

More preferably, the first and second surfaces are substantially parallel.

Preferably, the blisters in the first and second surfaces are configured such that the blisters in the first surface are disposed in one or both of spaces between and adjacent the blisters in the second surface.

In one embodiment the plurality of surfaces are defined by separate elements.

In another embodiment the plurality of surfaces are defined by a single element.

The present invention also provides a powder inhaler which comprises the above-described blister pack unit.

The present invention further provides a blister pack assembly which comprises the above-described blister pack unit and a suction tube which includes a cutting assembly which is configured for insertion into a respective one of the blisters and an inhalation channel through which powder is in use inhaled.

Preferably, the body of the blister pack unit includes a clip for holding the suction tube when not in use.

Preferably, the blister pack assembly further comprises an interconnecting member for connecting the suction tube to the blister pack unit so as to prevent the suction tube from being separated from the blister pack unit.

In a preferred embodiment the interconnecting member includes a line.

Preferably, the body of the blister pack unit includes a track and the interconnecting member includes an element which is captively disposed within the track and movable between first and second positions.

In a preferred embodiment the track is configured such that with the element of the interconnecting member in one of the first and second positions the interconnecting member is disposed substantially within the track.

The present invention still further provides a powder inhaler which comprises the above-described blister pack assembly.

Preferably, the powder inhaler further comprises a support unit for supporting the blister pack assembly, which support unit includes a plurality of openings for guiding the suction tube into respective blisters in the one of the plurality of surfaces adjacent thereto.

More preferably, the support unit comprises a housing in which the body of the blister pack unit is removably received, with at least one wall of the housing including the openings.

Still more preferably, the support unit further comprises a cover member which is hingeably mounted to the housing and encloses the suction tube and the openings when closed.

Medicaments suitable for use with the present invention are any which may be delivered by inhalation and include, for example, $\beta 2$-adrenoreceptor agonists, for example, salbutamol, terbutaline, rimiterol, fenoterol, reproterol, adrenaline, pirbuterol, isoprenaline, orciprenaline, bitolterol, salmeterol, formoterol, clenbuterol, procaterol, broxaterol, picumeterol, TA-2005, mabuterol and the like, and their pharmacologically acceptable esters and salts; anticholinergic bronchodilators, for example, ipratropium bromide and the like; glucocorticosteroids, for example, beclomethasone, fluticasone, budesonide, tipredane, dexamethasone, betamethasone, fluocinolone, triamcinolone acetonide, mometasone and the like, and their pharmacologically acceptable esters and salts; antiallergic medicaments, for example, sodium cromoglycate and nedocromil sodium; expectorants; mucolytics; antihistamines; cyclooxygenase inhibitors; leukotriene synthesis inhibitors; leukotriene antagonists; phospholipase-A2 (PLA2) inhibitors; platelet aggregating factor (PAF) antagonists and prophylactics of asthma; antiarrhythmic medicaments; tranquil isers; cardiac glycosides; hormones; antihypertensive medicaments; antidiabetic medicaments; antiparasitic medicaments; anticancer medicaments; sedatives; analgesic medicaments; antibiotics; antirheumatic medicaments; immunotherapies; antifungal medicaments; antihypotension medicaments; vaccines; antiviral medicaments; proteins; polypeptides and peptides, for example, peptide hormones and growth factors; polypeptide vaccines; enzymes; endorphines; lipoproteins and polypeptides involved in the blood coagulation cascade; vitamins; and others, for example, cell surface receptor blockers, antioxidants, free radical scavengers and organic salts of N,N'-diacetylcystine.

A preferred embodiment of the present invention will now be described hereinbelow by way of example only with reference to the accompanying drawings, in which:

FIG. 7(a) illustrates in enlarged scale a plan view of the support member of the blister pack unit of the blister pack assembly of FIG. 6;

FIG. 7(b) illustrates one side view of the support member of FIG. 7(a);

FIG. 7(c) illustrates the other side view of the support member of FIG. 7(a);

FIG. 7(d) illustrates one end view of the support member of FIG. 7(a);

FIG. 7(e) illustrates the other end view of the support member of FIG. 7(a);

FIG. 8(a) illustrates in enlarged scale a plan view of one of the blister pack elements of the blister pack assembly of FIG. 6;

FIG. 8(b) illustrates an underneath plan view of the blister pack element of FIG. 8(a);

FIG. 8(c) illustrates one side view of the blister pack element of FIG. 8(a);

FIG. 8(d) illustrates the other side view of the blister pack element of FIG. 8(a);

FIG. 8(e) illustrates one end view of the blister pack element of FIG. 8(a);

FIG. 8(f) illustrates the other end view of the blister pack element of FIG. 8(a);

FIG. 9(a) illustrates a plan view of the interconnecting member of the blister pack assembly of FIG. 6;

FIG. 9(b) illustrates a side view of the interconnecting member of FIG. 9(a);

Figure 1:
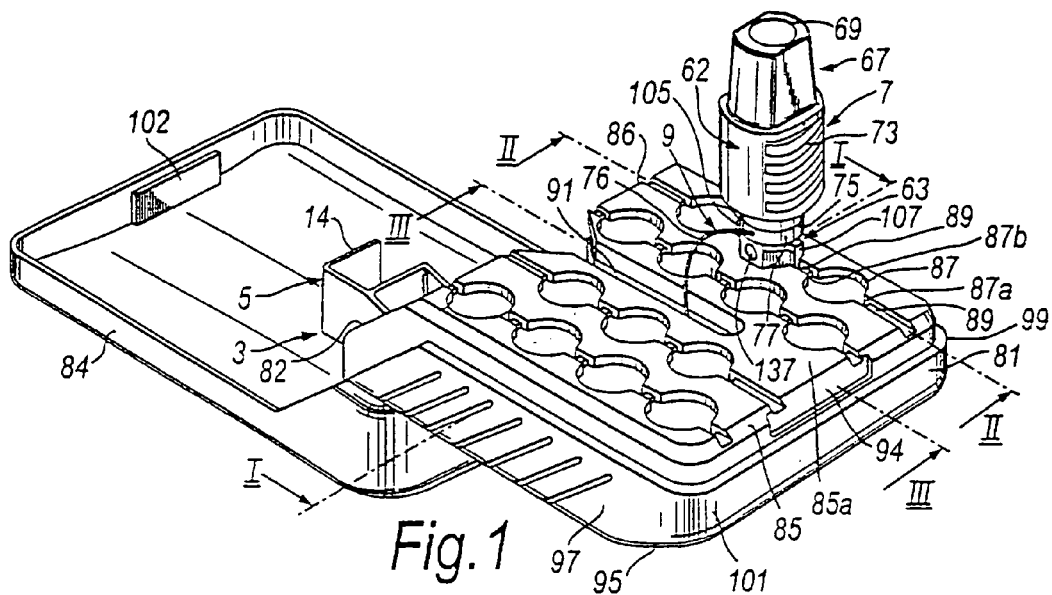
FIG. 1 illustrates in use a perspective view of an inhaler in accordance with a preferred embodiment of the present invention.
Figure 6:
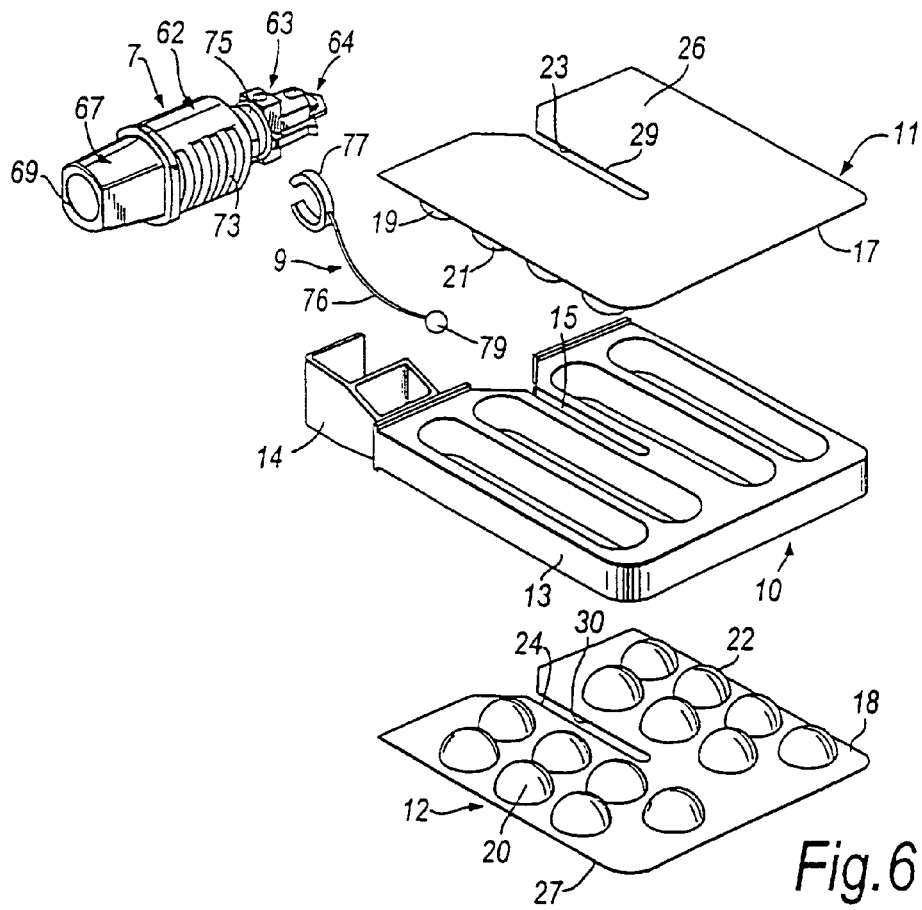
FIG. 6 illustrates an exploded perspective view of the blister pack assembly of the inhaler of FIG. 1.
Figure 2:
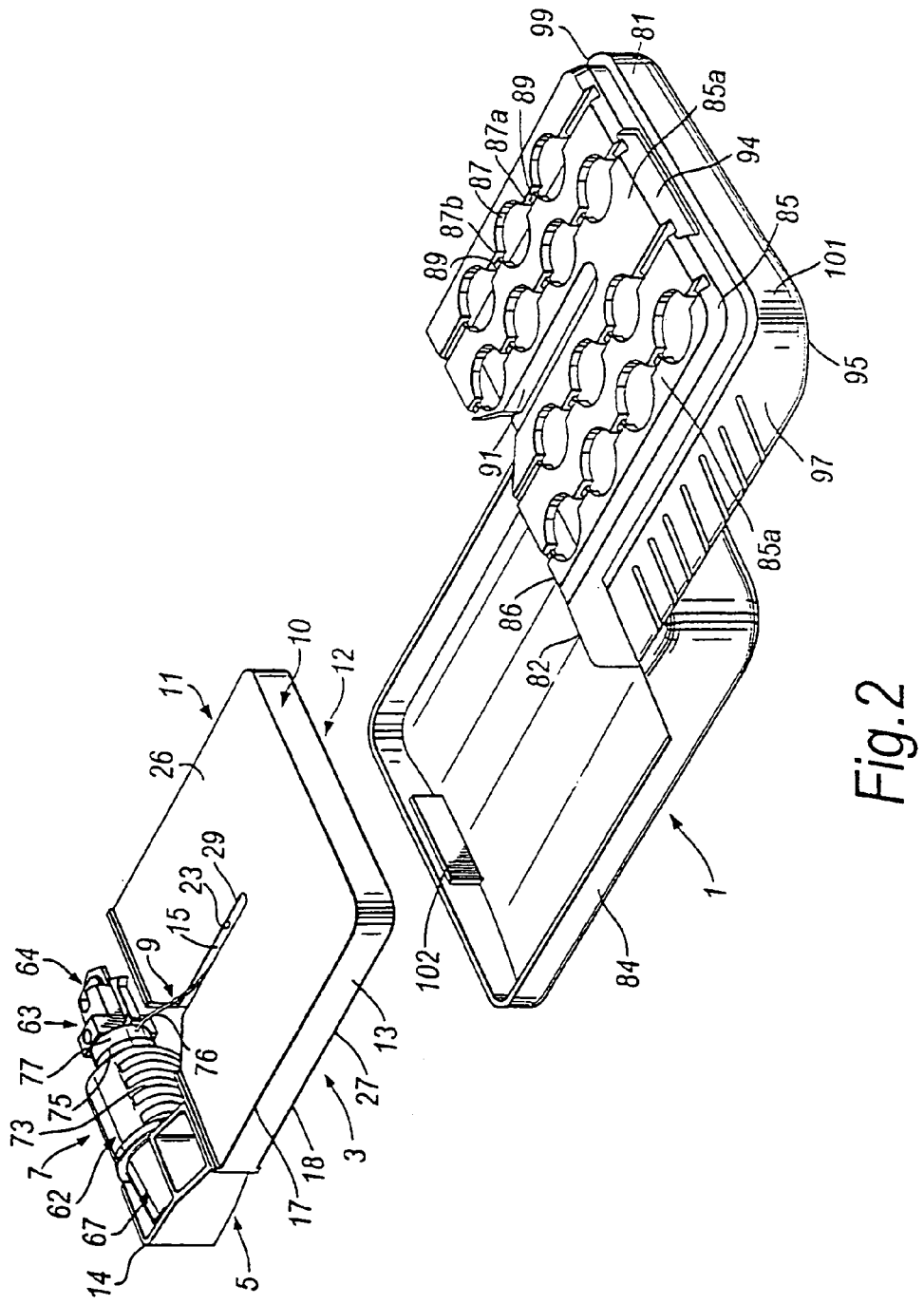
FIG. 2 illustrates an exploded perspective view of the inhaler of FIG. 1.
Figure 3:
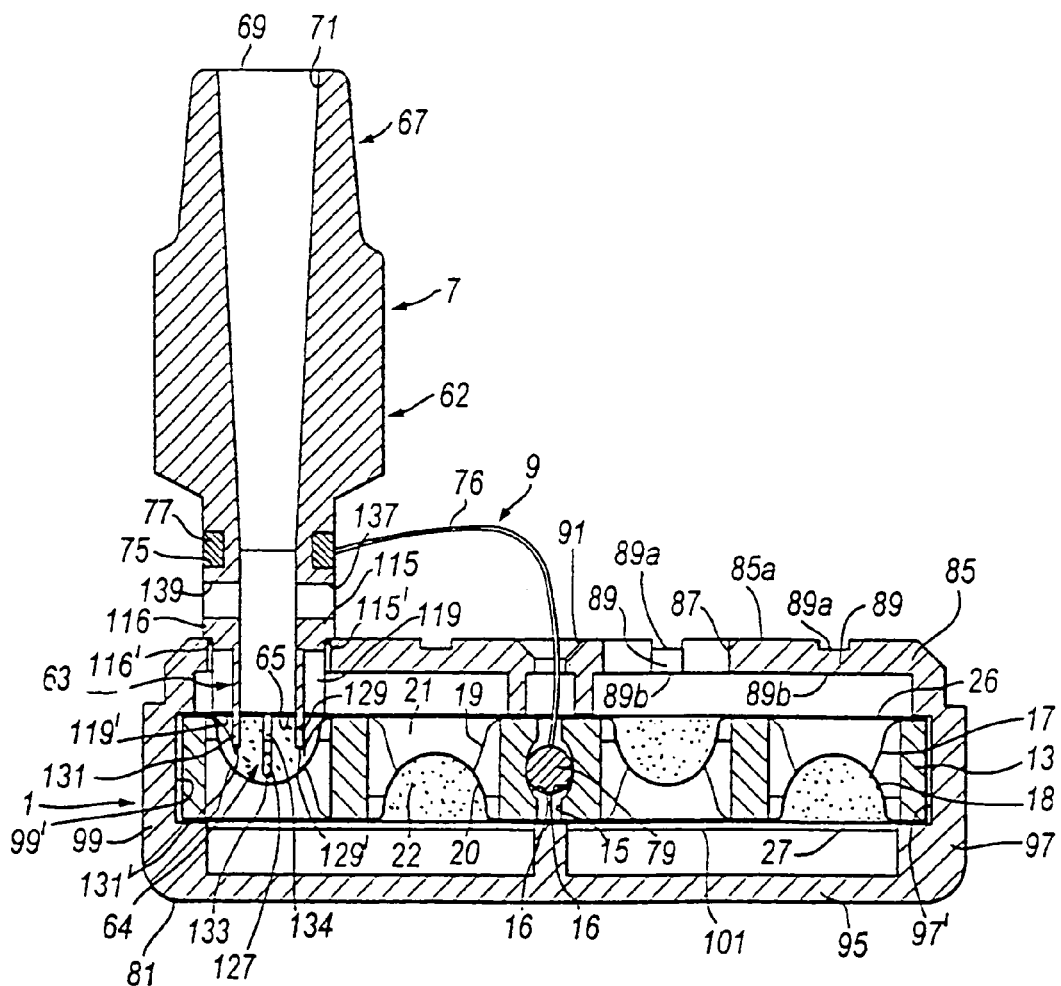
FIG. 3 illustrates in enlarged scale a vertical sectional view (along section I—I in FIG. 1) of the inhaler of FIG. 1.
Figure 4:
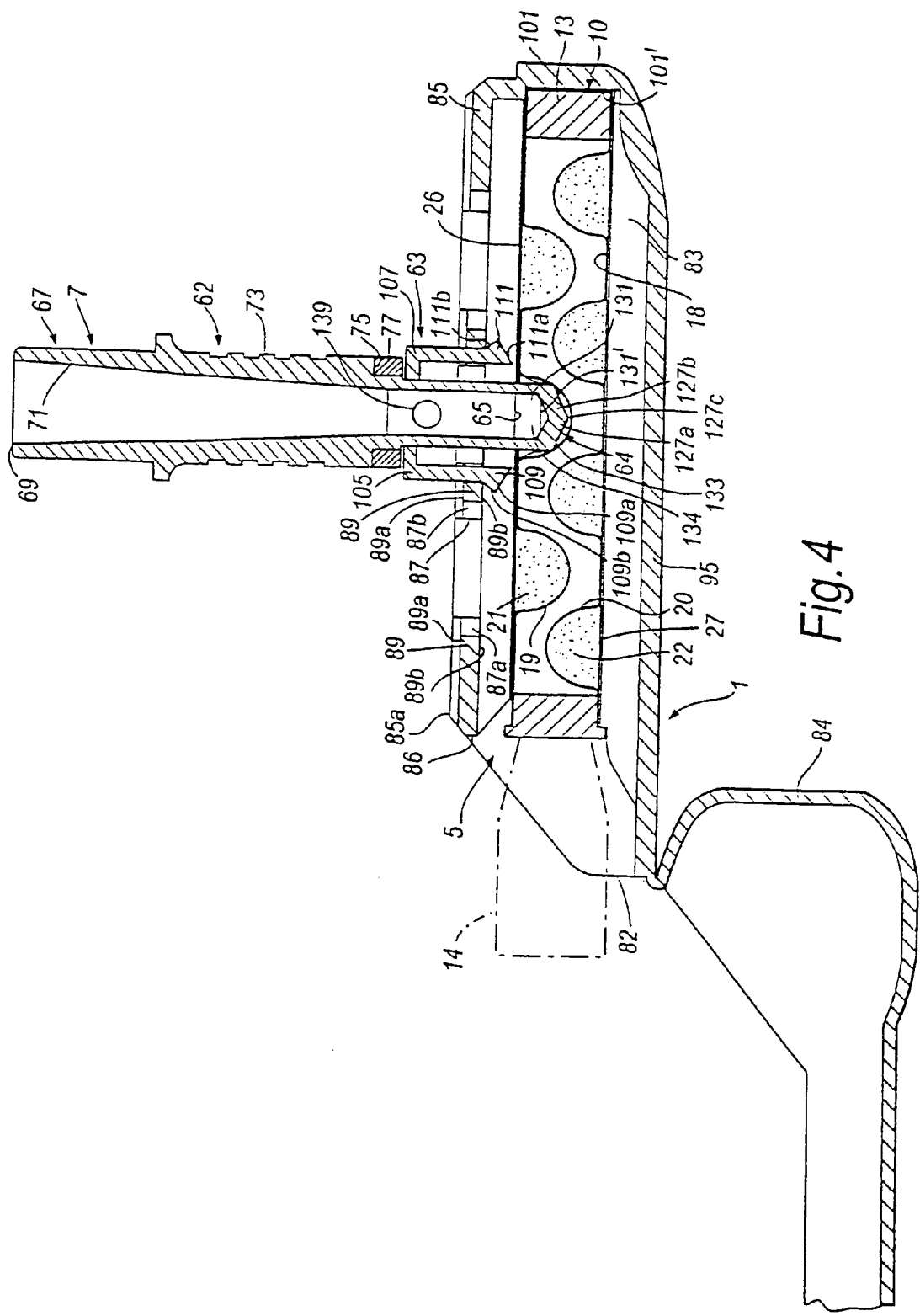
FIG. 4 illustrates in enlarged scale a fragmentary vertical sectional view (along section II—II in FIG. 1) of the inhaler of FIG. 1.
Figure 5:
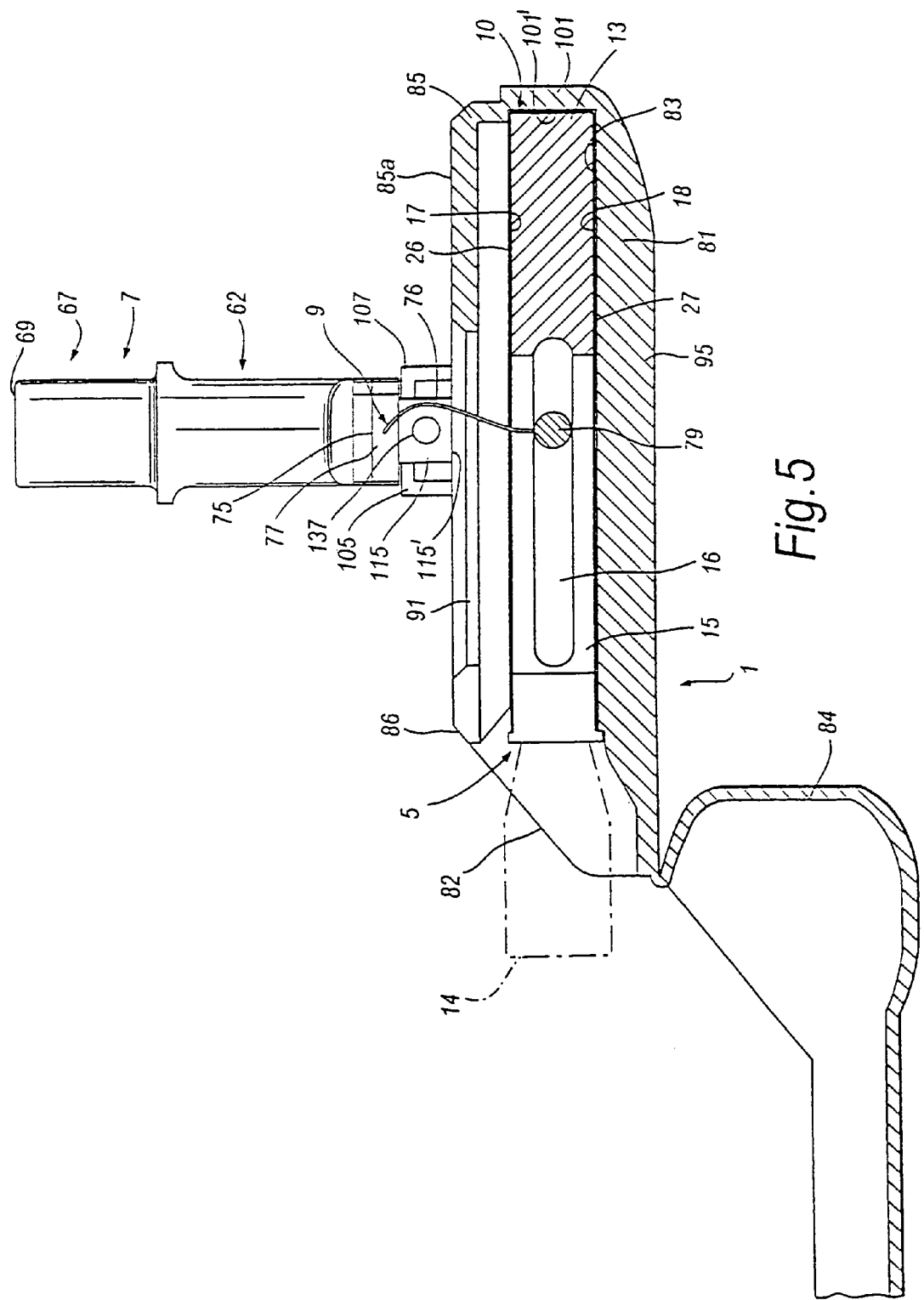
FIG. 5 illustrates in enlarged scale a fragmentary vertical sectional view (along section III—III in FIG. 1) of the inhaler of FIG. 1.
Figure 10A:
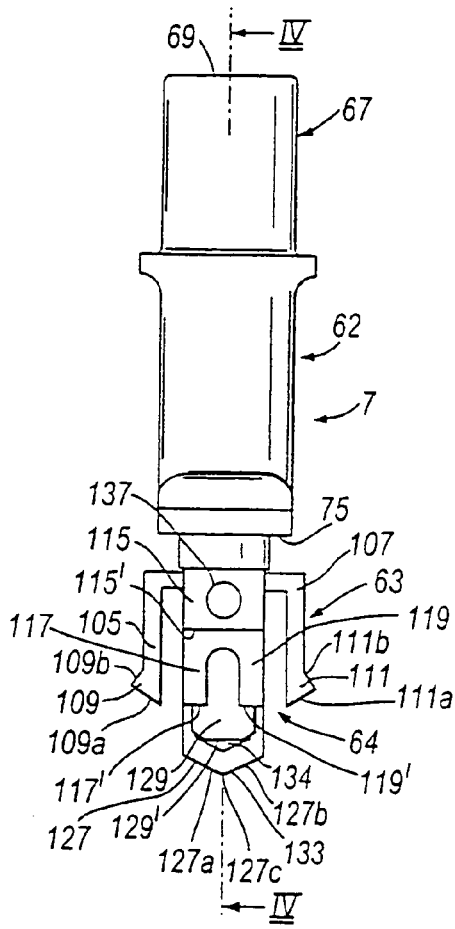
FIG. 10(a) illustrates in enlarged scale a first side view of the suction tube of the blister pack assembly of FIG. 6.
Figure 10B:
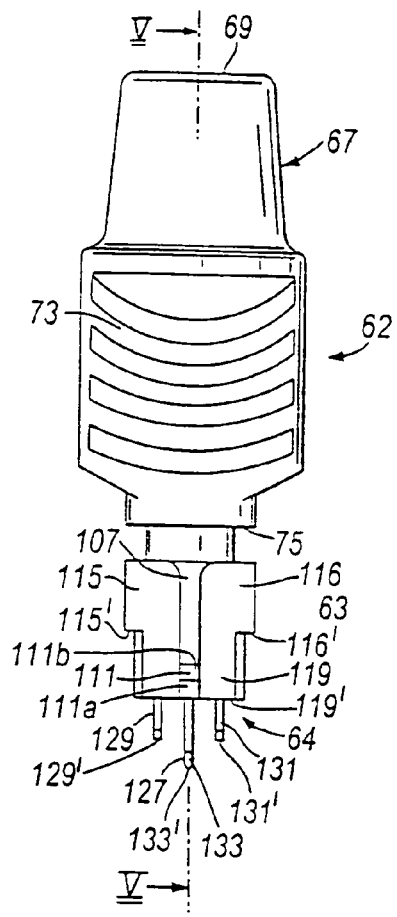
FIG. 10(b) illustrates a second, orthogonal side view of the suction tube of FIG. 10(a)
Figure 10C:
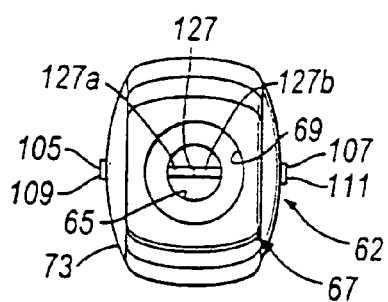
FIG. 10(c) illustrates a plan view of the suction tube of FIG. 10(a)
Figure 10D:
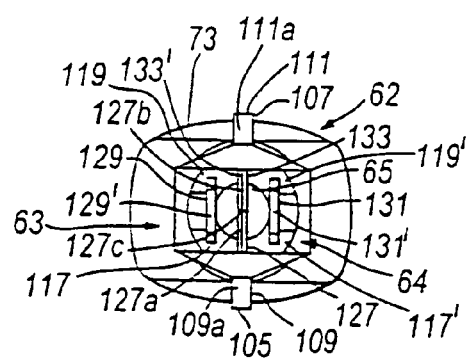
FIG. 10(d) illustrates an underneath plan view of the suction tube of FIG. 10(a)
Figure 10E:
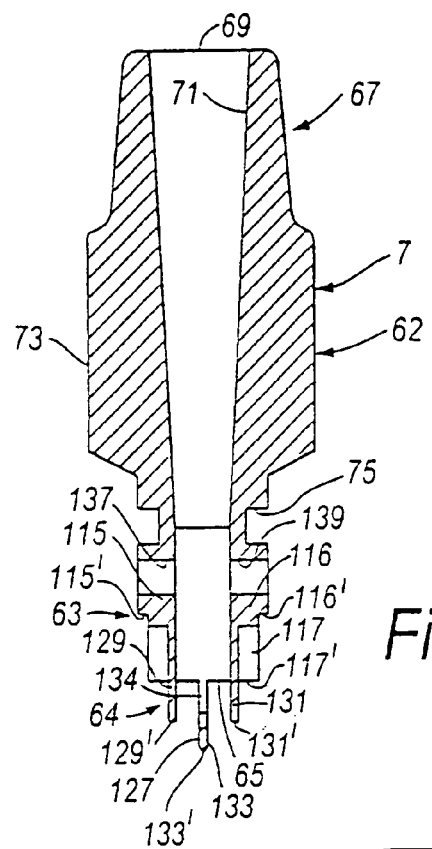
FIG. 10(e) illustrates a vertical sectional view (along section IV—IV in FIG. 10(a)) of the suction tube of FIG. 10(a)
Figure 10F:
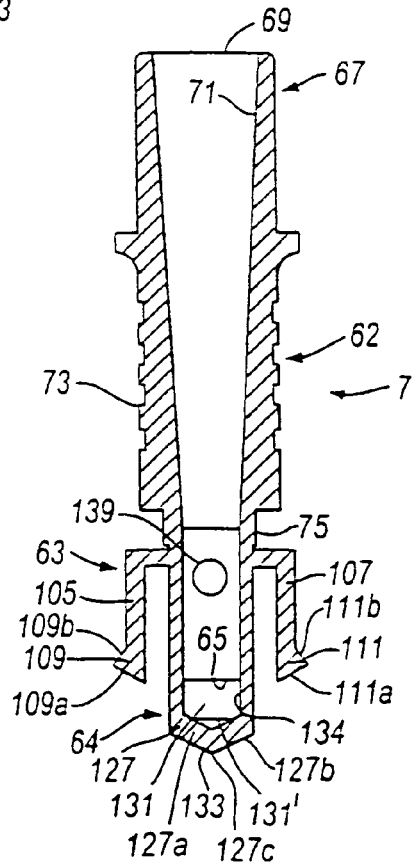
FIG. 10(f) illustrates a vertical sectional view (along section V—V in FIG. 10(b)) of the suction tube of FIG. 10(a)
Figure 11A:
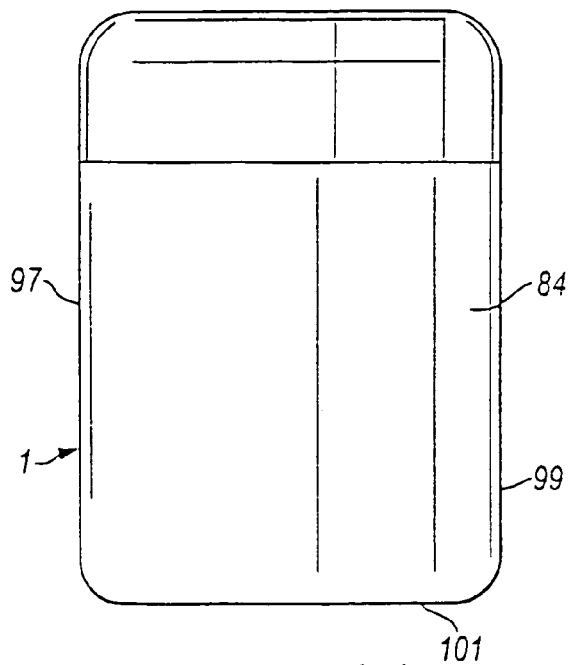
FIG. 11(a) illustrates a plan view of the support unit of the inhaler of FIG. 1, illustrated in the closed or storage configuration.
Figure 11B:
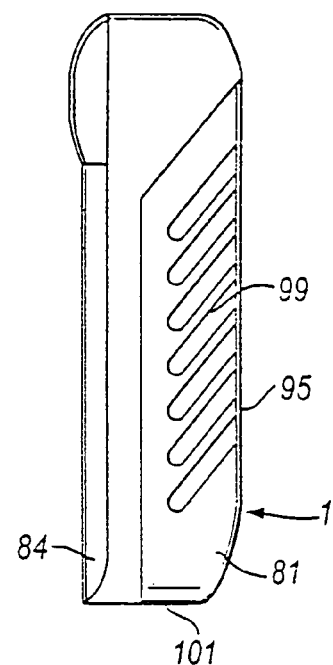
FIG. 11(b) illustrates a side view of the support unit of FIG. 11(a) illustrated in the closed or storage configuration.
Figure 11C:
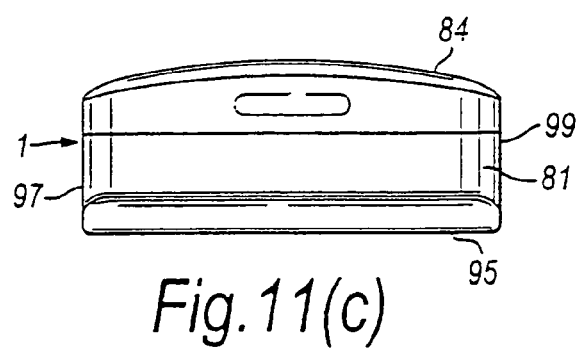
FIG. 11(c) illustrates one end view of the support unit of FIG. 11(a), illustrated in the closed or storage configuration.
Figure 11D:
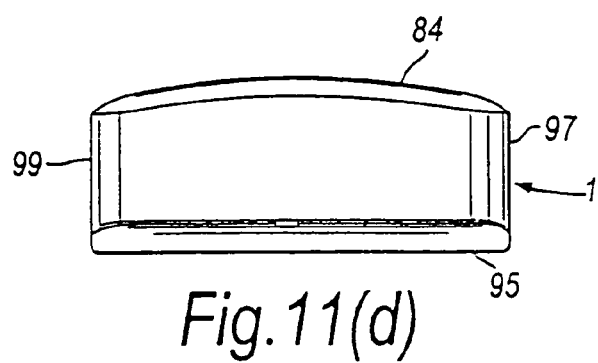
FIG. 11(d) illustrates the other end view of the support unit of FIG. 11(a), illustrated in the closed or storage configuration.
Figure 11E:
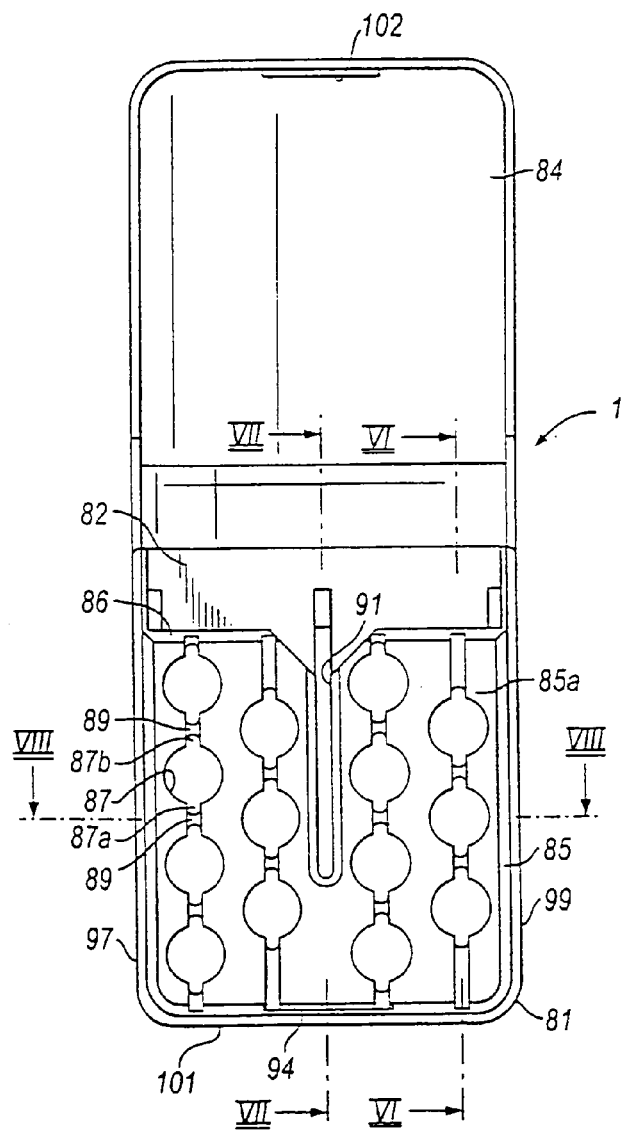
FIG. 11(e) illustrates a plan view of the support unit of FIG. 11(a), illustrated in the open or operative configuration.
Figure 11F:
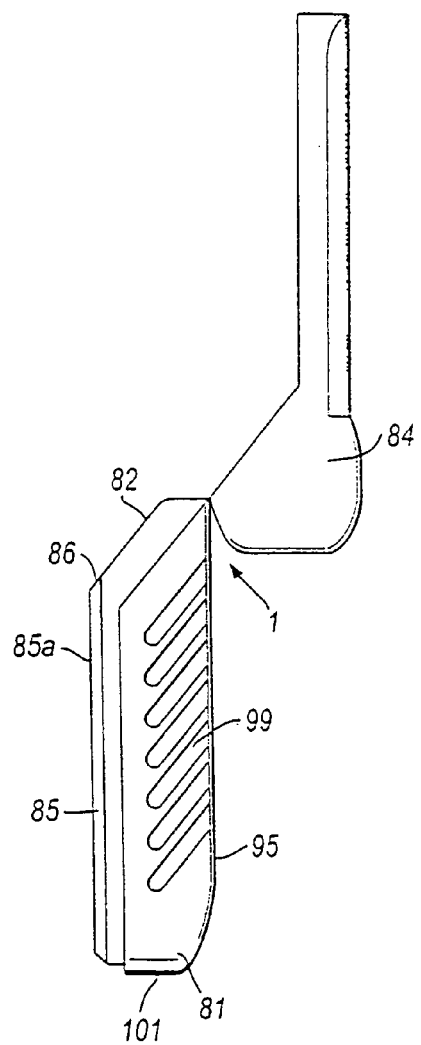
FIG. 11(f) illustrates a side view of the support unit of FIG. 11(a), illustrated in the open or operative configuration.
Figure 11G:
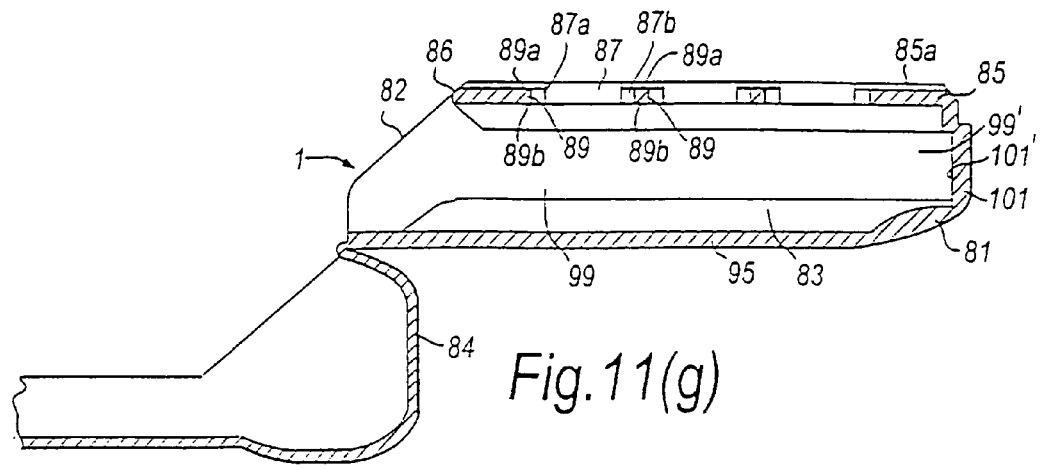
FIG. 11(g) illustrates in enlarged scale a fragmentary vertical sectional view (along section VI—VI in FIG. 11(e)) of the support unit of FIG. 11(a), illustrated in the open or operative configuration.
Figure 11H:
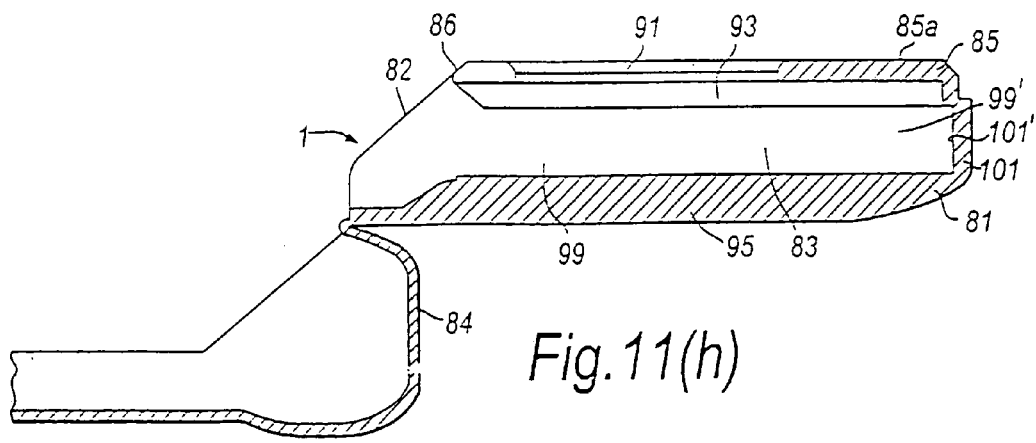
FIG. 11(h) illustrates in enlarged scale a fragmentary vertical sectional view (along section VII—VII in FIG. 11(e)) of the support unit of FIG. 11(a), illustrated in the open or operative configuration.
Figure 11I:
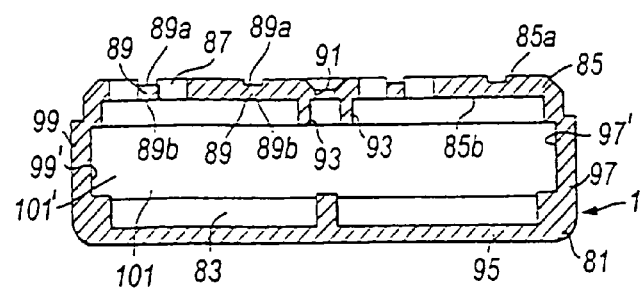
FIG. 11(i) illustrates in enlarged scale a vertical sectional view (along section VIII—VIII in FIG. 11(e)) of the support unit of FIG. 11(a), illustrated in the open or operative configuration.

The inhaler-comprises a support unit 1 and a blister pack assembly 3 which in use is fitted thereto.

The blister pack assembly 3 comprises a blister pack unit 5, a suction tube 7 and an interconnecting member 9 which connects the suction tube 7 to the blister pack unit 5 so as to prevent the suction tube 7 from being inadvertently separated from the blister pack unit 5.

The blister pack unit 5 comprises a support member 10 and first and second blister pack elements 11, 12 and, for example, by an adhesive, to the support member 10 so as to present first and second oppositely-directed parallel surfaces.

The support member 10 comprises a frame 13 to which the blister pack elements 11, 12 are fixed and a clip 14 at one edge of the frame 13 which is configured to hold the suction tube 7 when not in use. The frame 13 includes an elongate slot 15 which extends along the central axis from the one edge thereof, the opposing surfaces of which slot 15 include respective grooves 16 which define a closed track in which a mutually configured part of the interconnecting member 9 is captively disposed as will be described in more detail hereinbelow.

The first and second blister pack elements 11, 12 each comprise a substantially planar thin sheet 17, 18 which includes a plurality of cavities 19, 20, each defining a part of a respective blister 21, 22, and an elongate slot 23, 24 which extends along the central axis from one edge thereof such as to overlie the slot 15 in the frame 13 of the support member 10 when fitted thereto. In this embodiment the sheets 17, 18 are formed of a metal, such as aluminium, and the cavities 19, 20 have a depth of about 4 mm and a diameter at the opening thereof of about 7.5 mm. In alternative embodiments the sheets 17, 18 can be formed of a plastics material or a laminate of metal and plastics material.

The first and second blister pack elements 11, 12 each further comprise a thin film 26, 27 which is attached to the substantially planar surface of the sheet 17, 18 thereof so as to cover the openings of each of the cavities 19, 20 and thereby enclose a dose of powder containing medicament in each blister 21, 22. The films 26, 27 each include an elongate slot 29, 30 which extends along the central axis from one edge thereof such as to overlie the respective slots 23, 24 in the sheets 17, 18. In this embodiment the films 26, 27 are formed of a metal, such as aluminium, and are attached to the respective sheets 17, 18 by one of welding or an adhesive.

In this embodiment the first and second blister pack elements 11, 12 are identical and configured such that, when arranged back-to-back so as to present oppositely-directed blister surfaces, the cavities 19 in the first blister pack element 11 are located in spaces between and adjacent the cavities 20 in the second blister pack element 12. In this way, the thickness of the blister pack unit 5 and hence the inhaler is kept to a minimum for blisters 21, 22 of a particular dimension.

The suction tube 7, which will be described in further detail hereinbelow, comprises a generally elongate body 62 which includes an inlet section 63 at one end, which inlet section 63 includes a cutting assembly 64 for cutting the films 26, 27 covering the cavities 19, 20 of the blisters 21, 22 in the blister pack elements 11, 12 and an inlet 65 through which powder containing medicament is in use drawn from a respective blister 21, 22 on inhalation by a user, an outlet section 67 at the other end, which outlet section 67 includes an outlet 69 and provides a mouthpiece, and an inhalation channel 71 providing fluid communication between the inlet 65 and the outlet 69. The body 62 of the suction tube 7 includes at the outer surface thereof a plurality of ribs 73 for allowing a user to grip the same securely and a peripheral recess 75 for receiving a part of the interconnecting member 9 as will be described in more detail hereinbelow.

The interconnecting member 9 comprises a line 76 of a flexible material, preferably a plastics material, such as nylon, a clip 77 fixed to one end of the line 76 which is located in the peripheral recess 75 in the outer surface of the body 62 of suction tube 7 so as to anchor the line 76 to the same and an element 79 fixed at the other end of the line 76 which is of larger dimension than the gauge of the line 76 and is captively disposed in the slot 15 in the frame 13 of the support member 10. In this embodiment the clip 77 is part-circular and formed of a resilient material so as to be a snap-fit about the body 62 of the suction tube 7. With this configuration, the line 76 is anchored to the suction tube 7 but yet allows the suction tube 7 to rotate relative thereto. As will become apparent hereinbelow, the suction tube 7, in being rotatable relative to the clip 77 of the interconnecting member 9, has a much greater freedom of movement and thereby facilitates use.

The support unit 1 comprises a housing 81 which includes an opening 82 and defines a cavity 83 into which the blister pack unit 5 of the blister pack assembly 3 is in use inserted and a cover member 84 for enclosing the blister pack assembly 3 when not in use.

The housing 81 comprises a first, upper wall member 85 which, in this embodiment, is substantially planar. The upper wall member 85 includes an upper, outer surface 85a and a lower, inner surface 85b adjacent which one of the first and second blister pack elements 11, 12 of the blister pack unit 5 of the blister pack assembly 3 is in use disposed. The upper wall member 85 also includes one free end 86 which defines a part of the opening 82 in the housing 81 through which the blister pack unit 5 is in use inserted. The upper wall member 85 further includes a plurality of openings 87 which each overlie a respective one of the openings of the cavities 19, 20 of the blisters 21, 22 in the one of the first and second blister pack elements 11, 12 adjacent thereto such that each of the respective blisters 21, 22 can be emptied by inserting the suction tube 7 into a respective one of the openings 87. In this embodiment the openings 87 in the upper wall member 85 are each configured to have the same peripheral shape as the inlet section 63 of the suction tube 7 such that the openings 87 act as positive guides for guiding the inlet section 63 of the suction tube 7 into a respective blister 21, 22 in the one of the first and second blister pack elements 11, 12 adjacent thereto. Each of the openings 87 includes first and second radial extensions 87a, 87b for receiving mutually configured parts on the inlet section 63 of the suction tube 7 as will be described hereinbelow. The radial extensions 87a, 87b of the openings 87 each include a web member 89 which includes upper and lower surfaces 89a, 89b that are substantially parallel respectively to the upper and lower surfaces 85a, 85b of the upper wall member 85 of the housing 81. The web members 89 are of lesser thickness than the upper wall member 85 of the housing 81 and are disposed such that the upper surfaces 89a thereof are stepped back from the upper surface 85a of the upper wall member 85. The upper wall member 85 of the housing 81 further includes an elongate slot 91 which extends from the one free end 86 thereof, in this embodiment along the central axis of the housing 81, and overlies the slot 15 in the frame 13 of the support member 10 of the blister pack unit 5 when fitted such that the line 76 of the interconnecting member 9 can be drawn thereinto and pass freely therealong. The upper wall member 85 still further includes a plurality of elongate ribs 93 which extend downwardly from the lower surface 85b thereof parallel to the central axis of the housing 81. The ribs 93 are provided to ensure that the surface of the one of the first and second blister pack elements 11, 12 adjacent thereto is spaced from the lower surface 85a of the upper wall member 85 and thereby provide an air flow path to the blisters 21, 22 in the one of the first and second blister pack elements 11, 12 adjacent thereto. It will be appreciated that this configuration, in not having the line 76 of the interconnecting member 9 fixed at one point, is advantageous in that the line 76 of the interconnecting member 9 need only be as long as the distance between the furthestmost opening 87 and the elongate slot 91 in the upper wall member 85, which distance, in this embodiment, corresponds to approximately half of the width of the upper wall member 85. The upper wall member 85 still further includes a recess 94 at that end thereof remote from the opening 82 in the housing 81.

The housing 81 further comprises a second, lower wall member 95, in this embodiment substantially planar, which is spaced in parallel relation to the upper wall member 85, first and second side wall members 97, 99 which extend between the sides of the upper and lower wall members 85, 95 and an end wall member 101 which extends between the ends of the upper and lower wall members 85, 95 remote from the opening 82 in the housing 81. In this embodiment the side wall members 97, 99 and the end wall member 101 each include a channel 97', 99', 101' into which the peripheral edge at the sides and the other end of the blister pack unit 5 of the blister pack assembly 3 is in use located such that one of the first and second blister pack elements 11, 12 is held in position adjacent the lower surface 85b of the upper wall member 85 of the housing 81.

The cover member 84 is hinged to the housing 81, in this embodiment at that end adjacent the opening 82 therein. In a preferred embodiment the housing 81 and the cover member 84 of the support unit 1 are integrally formed of a plastics material such that the hinged connection of the housing 81 and the cover member 84 is provided by a living hinge. The cover member 84 includes a catch member 102 at the free end thereof which is configured to engage the recess 94 in the upper wall member 85 of the housing 81 when the cover member 84 is closed and thereby hold the same closed.

As described hereinabove, the suction tube 7 includes an inlet section 63 which includes a cutting assembly 64 for cutting the films 26, 27 covering the cavities 19, 20 of the blisters 21, 22 in the first and second blister pack elements 11, 12.

The inlet section 63 of the suction tube 7 further includes first and second arms 105, 107 which extend forwardly, in the sense of insertion of the suction tube 7 into a blister 21, 22 in a respective one of the first and second blister pack elements 11, 12, from respective sides thereof and are biased outwardly. The arms 105, 107 are each configured so as to be a sliding fit in the radial extensions 87a, 87b of the openings 87 in the upper wall member 85 of the housing 81. In this way, the suction tube 7 can only be inserted into an opening 87 in the upper wall member 85 of the housing 81 in one of two orientations and, as will become apparent hereinbelow, since the cutting assembly 64 has two-fold rotational symmetry, the suction tube 7 can never inadvertently be inserted into a blister 21, 22 with another orientation which may cause the film 26, 27 covering the respective blister 21, 22 to be cut free. It will, of course, be appreciated that in any embodiment where the cutting assembly 64 of the suction tube 7 does not have such rotational symmetry, the first and second arms 105, 107 at the inlet section 63 and the radial extensions 87a, 87b of the openings 87 in the upper wall member 85 of the housing 81 can be configured so as to permit the suction tube 7 to be inserted into the openings 87 in the upper wall member 85 of the housing 81 in only one orientation. Each of the first and second arms 105, 107 includes a catch member 109, 111 which is configured to engage with the web members 89 in the radial extensions 87a, 87b of the openings 87 in the upper wall member 85 of the housing 81. The catch members 109, 111 on the first and second arms 105, 107 each have a first surface 109a, 111a which has a forwardly-directed component and acts as a guiding surface and a second surface 109b, 111b which has a rearwardly-directed component and acts as a locking surface. In use, on fitting the suction tube 7 to the housing 81, the second, locking surfaces 109b, 111b of the catch members 109, 111 snap behind respective ones of the lower surfaces 89b of the web members 89 in the radial extensions 87a, 87b of the openings 87 in the upper wall member 85 of the housing 81 so as to prevent the suction tube 7 from falling out of the respective opening 87 and thereby avoid the need for the user continuously to hold the suction tube 7 in position. It will be appreciated that the catch members 109, 111, in being a snap fit, provide the user with a clear indication that the suction tube 7 is correctly fitted to the housing 81 and hence inserted into a respective one of the blisters 21, 22 in the one of the first and second blister pack elements 11, 12 adjacent thereto. In this regard, the second, locking surfaces 109b, 111b of the catch members 109, 111 are configured so as to allow the suction tube 7 to be removed from a respective one of the openings 87 in the upper wall member 85 of the housing 81 after use on the application of a light force.

The inlet section 63 of the suction tube 7 yet further includes first and second lugs 115, 116 which extend radially therefrom and each include a lower surface 115', 116' which defines a first shoulder that acts to limit the extent to which the suction tube 7 can be inserted into any of the openings 87 in the upper wall member 85 of the housing 81 and hence a respective blister 21, 22 in the one of the first and second blister pack elements 11, 12 adjacent thereto. In this embodiment the lugs 115, 116 are configured such that the shoulder defined by the lower surfaces 115', 116' thereof abuts the upper surface 85a of the upper wall member 85 of the housing 81 on the required insertion of the suction tube 7 into one of the openings 87 in the upper wall member 85 of the housing 81. In this way, the suction tube 7 cannot be inserted too far into a blister 21, 22 which could result in the cutting assembly 64 at the inlet section 63 of the suction tube 7 being forced inadvertently through the cavity 19, 20 of any blister 21, 22 on fitting the suction tube 7 to the housing 81.

The inlet section 63 of the suction tube 7 still further includes first and second axially-extending members 117, 119 which each include a lower surface 117', 119' that defines a second shoulder which is axially forward, in the sense of inserting the suction tube 7 into one of the openings 87 in the upper wall member 85 of the housing 81, of the first shoulder defined by the lower surfaces 15', 116' of the lugs 115, 116. In this embodiment the first and second axially-extending members 117, 119 are configured such that the second shoulder defined by the lower surfaces 117', 119' thereof abuts the upper surface of the one of the first and second blister pack elements 11, 12 adjacent thereto when the first shoulder defined by the lower surfaces 115', 116' of the lugs 115, 116 abuts the upper surface 85a of the upper wall member 85 of the housing 81.

The cutting assembly 64 of the inlet section 63 of the suction tube 7 comprises a cutting blade 127 and first and second ram blades 129, 131 disposed adjacent thereto.

The cutting blade 127 includes a cutting edge 133 which extends across and is located axially forward, in the sense of inserting the suction tube 7 into one of the openings 87 in the upper wall member 85 of the housing 81, of the inlet 65 of the suction tube 7 such that, on insertion of the suction tube 7 into one of the openings 87 in the upper wall member 85 of the housing 81, a cut is made in the film 26, 27 covering the opening of the cavity 19, 20 of the blister 21, 22 therebeneath. In this embodiment the cutting edge 133 of the cutting blade 127 includes a cutting point 133'. The cutting blade 127, which in this embodiment is substantially planar, is co-axial with the longitudinal axis of the body 62 of the suction tube 7 and includes first and second flank sections 127a, 127b which taper to an axially-foremost cutting point 127c located on the longitudinal axis of the body 62 of the suction tube 7. In this embodiment the flank sections 127a, 127b of the cutting blade 127 enclose an angle of about 120 degrees. The cutting blade 127 has an effective cutting length approaching that of the diameter of the openings to the cavities 19, 20 of the blisters 21, 22 in the blister pack elements 11, 12 such that, on insertion of the suction tube 7 into a respective one of the openings 87 in the upper wall member 85 of the housing 81, the cutting blade 127 cuts the film 26, 27 across the diameter of the opening to the cavity 19, 20 of the respective blister 21, 22. The cutting blade 127 further includes a transverse opening 13A located behind the cutting edge 133 thereof for providing an air flow path therethrough.

The first and second ram blades 129, 131, which in this embodiment are each substantially planar, are located to each side of the cutting blade 127 and, as will be described in more detail hereinbelow, are configured to bear on and push back the film 26, 27 covering the cavity 19, 20 of a respective one of the blisters 21, 22 once cut by the cutting blade 127 and thereby open the blister 21, 22. In this embodiment the first and second ram blades 129, 131 are disposed parallel to, and are the same radial distance from, the curting blade 127. The first and second ram blades 129, 131 each include a lower, axially-forward surface 129', 131' which is located axially rearward of the axially foremost part of the cutting edge 133 of the cutting blade 127 such that the ram blades 129, 131 act on the film 26, 27 only once at least partly cut by the cutting blade 127. In this embodiment the bearing surface 129', 131' of each of the ram blades 129, 131 is substantially flat.

In a preferred embodiment the cutting assembly 64 is configured such that the effective length of each of the bearing surfaces 129', 131' of the ram blades 129, 131, that is, the distance between the endmost points of the bearing surface 129', 131' of each of the ram blades 129, 131, is approximately the same distance as the distance between the adjacent endmost points of the bearing surfaces 129', 131' of the ram blades 129, 131 and the endmost points of the effective cutting length of the cutting blade 127. In this way, the film 26, 27 covering the openings of the cavities 19, 20 of any of the blisters 21, 22 in the blister pack elements 11, 12 will be broken into flaps 136a-f of substantially equal size.

Figure 12A:
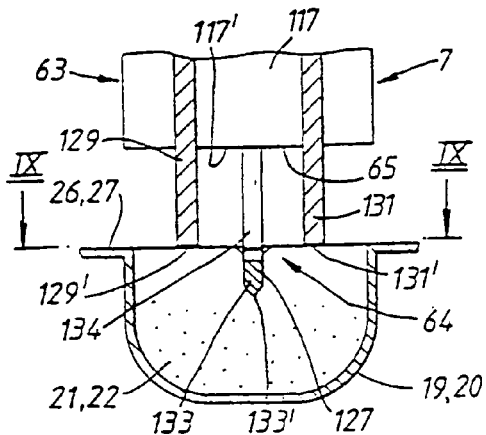
FIG. 12(a) illustrates a fragmentary vertical sectional view (along section IV—IV in FIG. 10(a)) of the suction tube of FIG. 10(a) when partly inserted into a blister.
Figure 12B:
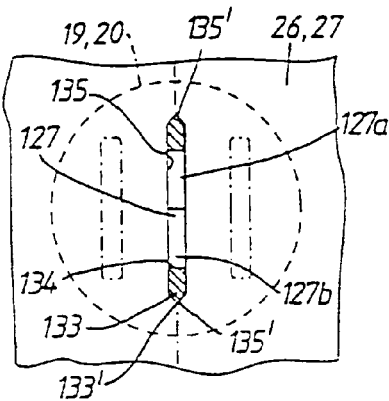
FIG. 12(b) illustrates a horizontal sectional view (along section IX—IX in FIG. 12(a)) of the suction tube of FIG. 10(a) when partly inserted into a blister.
Figure 13A:
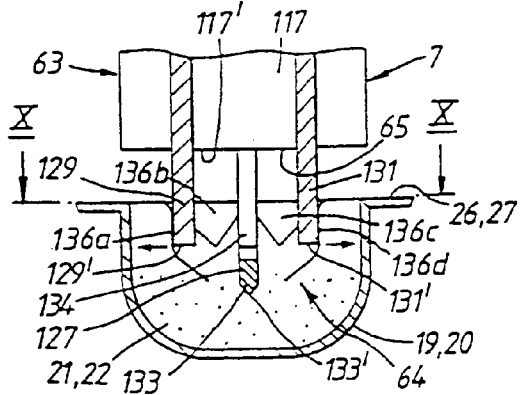
FIG. 13(a) illustrates a fragmentary vertical sectional view (along section IV—IV in FIG. 10(a)) of the suction tube of FIG. 10(a) when further inserted into a blister.
Figure 13B:
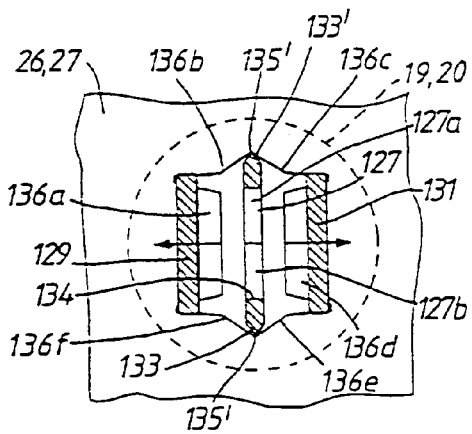
FIG. 13(b) illustrates a horizontal sectional view (along section X—X in FIG. 13(a)) of the suction tube of FIG. 10(a) when further inserted into a blister.
Figure 14A:
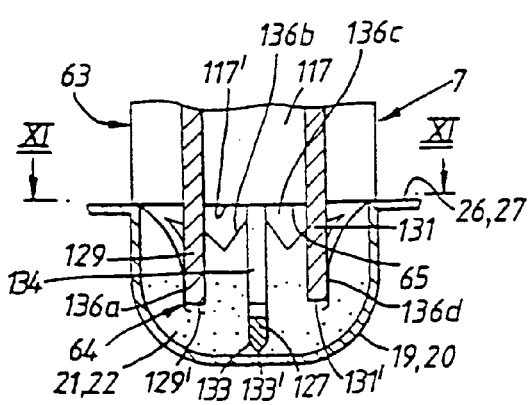
FIG. 14(a) illustrates a fragmentary vertical sectional view (along section IV—IV in FIG. 10(a)) of the suction tube of FIG. 10(a) when fully inserted into a blister.
Figure 14B:
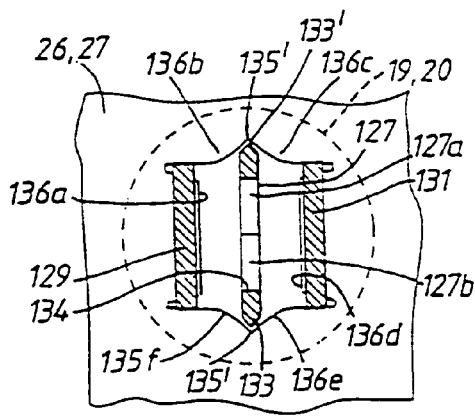
FIG. 14(b) illustrates a horizontal sectional view (along section XI—XI in FIG. 14(a)) of the suction tube of FIG. 10(a) when fully inserted into a blister.

The action of the cutting assembly 64 at the inlet section 63 of the suction tube 7 is clearly illustrated in FIGS. 12 to 14. In a first step, as illustrated in FIGS. 12(a) and 12(b), as the cutting assembly 64 is inserted into a blister 21, 22 the cutting blade 127 makes a cut 135 across the diameter of the film 26, 27 covering the opening of the cavity 19, 20 of the blister 21, 22. In a second step, as illustrated in FIGS. 13(a) and 13(b), as the cutting assembly 64 is inserted further into the blister 21, 22 the bearing surfaces 129', 131' of the ram blades 129, 131 act on the film 26, 27 and cause the film 26, 27 to tear between adjacent endmost points of the bearing surface 129', 131' of the ram blades 129, 131 and the ends 135' of the cut 135 so as to form six flaps 136a-f. As mentioned hereinabove, in a preferred embodiment the cutting blade 127 and the ram blades 129, 131 are configured such that the flaps 136a-f are of substantially equal size. In a final step, as illustrated in FIGS. 14(a) and 14(b), the cutting assembly 64 is inserted further into the blister 21, 22 until the second shoulder defined by the lower surfaces 117', 119' of the axially-directed members 117, 119 is at the upper surface of the one of the first and second blister pack elements 11, 12 adjacent thereto. In this position the suction tube 7 is inserted fully into the blister 21, 22. In inserting the cutting assembly 64 further into the blister 21, 22 the ram blades 129, 131 cause the flaps 136a-f to be pushed to the wall of the cavity 19, 20 of the blister 21, 22 so as to provide a large opening in the film 26, 27 covering the blister 21, 22 which allows for the ready withdrawal of powder therefrom.

The inlet section 63 of the suction tube 7 still yet further includes first and second upper supplementary air inlet openings 137, 139 into the inhalation channel 71 of the suction tube 7. The first and second upper supplementary air inlet openings 137, 139 into the inhalation channel 71 provide supplementary air flow paths, which, on inhalation by a user, allow supplementary air to be drawn into the inhalation channel 71 and mix with the air and powder mixture drawn through the inhalation channel 71 from a blister 21, 22. As will be appreciated, the provision of such supplementary air flow paths provides that for each unit volume of air inhaled the user inhales a reduced amount of powder containing medicament. Furthermore, the action of supplementary air mixing with an air and powder mixture drawn through the inhalation channel 71 induces turbulence and assists in the deagglomeration of that powder.

In use, a user first inserts a blister pack assembly 3 into the cavity 83 in the housing 81 of the support unit 1, with one of the blister pack elements 11, 12, in this embodiment the first blister pack element 11, adjacent the inner surface 85b of the upper wall member 85 of the housing 81. The user then unclips the suction tube 7 from the clip 14 of the support member 10 and inserts the inlet section 63 of the suction tube 7 through a respective opening 87 in the upper wall member 85 of the housing 81 and into an unused blister 21 therebeneath; with the opening 87 acting as a guide and the cutting assembly 64 of the suction tube 7 rupturing the film 26 covering the respective blister 21. With the inlet section 63 of the suction tube 7 located in the blister 21, the user then grips the outlet section 67 of the suction tube 7 in the lips and inhales so as to withdraw the dose of powder from the blister 21 and deliver the same into the lungs. After inhalation, the user clips the suction tube 7 back in the clip 14. This pattern of use can be repeated until all of the blisters 21 in the first blister pack element 11 have been used. When all of the blisters 21 in the first blister pack element 11 have been used, the user then withdraws the blister pack assembly 3 from the housing 81, rotates the same through 180 degrees about the axis of insertion and re-inserts the blister pack unit 5 of the blister pack assembly 3 into the cavity 83 in the housing 81, with the second blister pack element 12 adjacent the lower surface 85b of the upper wall member 85 of the housing 81 in which the openings 87 are provided. In this way, the blisters 22 in the second blister pack element 12 are available for use. When all of the blisters 22 in the second blister pack element 12 have been used, the user then withdraws the blister pack assembly 3 from the housing 81, disposes of the same and inserts a new blister pack assembly 3 into the cavity 83 in the housing 81. Where the blisters 21 in the first blister pack element 11 contain a different medicament to the blisters 22 in the second blister pack element 12, the blister pack assembly 3 is withdrawn, rotated and re-inserted as and when required to expose the respective blisters 21, 22 for use.

Finally, it will be understood by a person skilled in the art that the present invention is not limited to the described embodiment but can be modified in many different ways without departing from the scope of the invention as defined in the appended claims.

In one alternative embodiment the first and second blister pack elements 11, 12 could be provided as sections of a single element which includes a hinge section therebetween, with the single element being folded about the hinge section so as to present the first and second blister pack elements 11, 12 as oppositely-directed parallel surfaces when fitted to the support member 10.

In other alternative embodiments the blister pack unit 5 could include three or more blister pack elements, for example, any of three to six blister pack elements each being arranged as a surface of a respective triangular, square, pentagonal or hexagonal structure, with the housing 81 of the support unit 1 being modified accordingly.

What is claimed is:

1. A blister pack device for a powder inhaler comprising a blister pack having a body which includes first and second surfaces which are substantially parallel to each other and are spaced from each other, the first and second surfaces having a plurality of blisters containing medicament, wherein the blisters in the first and second surfaces are arranged in rows running parallel to the longitudinal axis of the blister pack and the blisters in each row in the first surface are configured to sit between the blisters in a co-operating row in the second surface, the blisters in the first and second surfaces being rotationally symmetrically disposed about the longitudinal axis of the blister pack and further comprising a support unit for enclosing the blister pack, said longitudinal axis being parallel to said first and second surfaces, said support unit including a plurality of openings in one surface which correspond with the blisters in the first or second surface adjacent thereto regardless of which way the user inserts the blister pack into said support unit, said blister pack being insertable into said support unit in one of two positions in which either the blisters in the first surface or the blisters in the second surface align with the openings in said support unit.

2. A blister pack device for a powder inhaler as claimed in claim 1, wherein the blisters in one row of a surface are off-set/staggered with respect to the blisters in an adjacent row of that surface.

3. A blister pack device as claimed in claim 1, wherein the blisters in the first and second surfaces are configured such that the blisters in the first surface are disposed in one or both of spaces between and adjacent the blisters in the second surface.

4. A blister pack device as claimed in claim 1, wherein the first and second surfaces are defined by separate elements.

5. A blister pack device as claimed in claim 1, wherein the first and second surfaces are defined by a single element.

6. A blister pack device as claimed in claim 1, further comprising a support member which supports the first and second surfaces.

7. A blister pack device as claimed in claim 6, wherein the support member comprises a frame.

8. A blister pack arrangement comprising the blister pack device of claim 6 and a suction tube which includes a cutting assembly which is configured for insertion into a respective one of the blisters and an inhalation channel through which powder is in use inhaled.

9. The blister pack arrangement of claim 8, wherein the body includes a clip for holding the suction tube when not in use.

10. The blister pack arrangement of claim 9, further comprising an interconnecting member for connecting the suction tube to the blister pack device so as to prevent the suction tube from being separated from the blister pack device.

11. The blister pack arrangement of claim 10, wherein the interconnecting member includes a line.

12. The blister pack arrangement of claim 10, wherein the body of the blister pack device includes a track and the interconnecting member includes an element which is captively disposed within the track and moveable between first and second positions.

13. The blister pack arrangement of claim 12, wherein the track is configured such that with the element of the interconnecting member in one of the first and second positions the interconnecting member is disposed substantially with the track.

14. A powder inhaler comprising the blister pack arrangement of claim 8.

15. The powder inhaler of claim 14, wherein the support unit comprises a housing in which the blister pack is removably received, with a least one wall of the housing including the openings.

16. The powder inhaler of claim 15, wherein the support unit further comprises a cover member which is hingeably mounted to the housing and encloses the suction tube and the openings when closed.

* * * * *